United States Patent [19]

Coe

[11] Patent Number: 5,917,087

[45] Date of Patent: Jun. 29, 1999

[54] PROCESS FOR PRODUCING SODIUM 1-THYROXINE COMPRISING THE OXIDATIVE COUPLING OF A DIIDO-1-TYROSINE CATALYSED BY A MANGANESE SALT IN THE PRESENCE OF AN AMINE

[75] Inventor: Paul Frederick Coe, Nottingham, United Kingdom

[73] Assignee: Knoll Aktiengesellschaft, Ludwigshafen, Germany

[21] Appl. No.: 08/817,325

[22] PCT Filed: Oct. 12, 1995

[86] PCT No.: PCT/EP95/04017

§ 371 Date: Apr. 7, 1997

§ 102(e) Date: Apr. 7, 1997

[87] PCT Pub. No.: WO96/11904

PCT Pub. Date: Apr. 25, 1996

[30] Foreign Application Priority Data

Oct. 14, 1994 [GB] United Kingdom .................... 9420705

[51] Int. Cl.$^6$ .................................................. C07C 229/00
[52] U.S. Cl. .............................................. 562/447; 560/39
[58] Field of Search ............................................. 502/447

[56] References Cited

U.S. PATENT DOCUMENTS

| | | | |
|---|---|---|---|
| 2,435,947 | 2/1948 | Turner et al. | 562/447 |
| 2,889,363 | 6/1959 | Ginger et al. | |
| 2,889,364 | 6/1959 | Anthony et al. | 502/447 |

FOREIGN PATENT DOCUMENTS 62-184023  8/1987  Japan.
52-71404  10/1993  Japan.

OTHER PUBLICATIONS

J. of Am. Chem. Soc., vol. 88, No. 5, 1996, pp. 1074–1076.
Proc. Soc. Exp. Biol. and Med., vol. 130, No. 2, 1969, pp. 556–563.
Z. Physiol. Chem., vol. 261, 1939, pp. 253–256 Chem. Abst. 1940, p. 1338.
Biochem. J., vol.43, 1948, pp. 223–231.
Biochem J., vol. 70, 1958, pp. 173–176.
Arch. Biochem. Biophys., vol. 140, 1970, pp. 90–95.

Primary Examiner—Paul J. Killos
Attorney, Agent, or Firm—Keil & Weinkauf

[57] ABSTRACT

Improvements to a six stage process for production of sodium l-thyroxine from l-tyrosine [described in U.S. Pat. No. 2,889,363 and U.S. Pat. No. 2,889,364 (Baxter)] are described, the improvements comprising the oxidative coupling of a diiodo-l-thyrosine to form a biphenyl ether derivative, catalysed by a manganese salt in which the amine and acid functionally of the diiodo-l-thyrosine have been protected by suitable protecting groups, characterised in that the reaction is performed at a pressure of about 20 atmospheres in the presence of an organic amine additive using a gaseous oxidant comprising oxygen and optionally an inert diluent. The process optionally further comprises acid hydrolysis of the biphenyl ether derivative with hydrochloric acid to form a l-thyroxine hydrochloride salt and generation of sodium-l-thyroxine from the l-thyroxine hydrochloride salt.

13 Claims, No Drawings

PROCESS FOR PRODUCING SODIUM 1-THYROXINE COMPRISING THE OXIDATIVE COUPLING OF A DIIDO-1-TYROSINE CATALYSED BY A MANGANESE SALT IN THE PRESENCE OF AN AMINE

The present invention relates to improvements in a process for producing sodium l-thyroxine, which is a thyroid hormone used to treat conditions such as myoedema, cretinism and obesity.

Sodium-l-thyroxine (which is the sodium salt of O-(4-hydroxy-3,5-diiodo-phenyl)-3,5-diiodo-l-tyrosine) can be produced in a six step synthesis as described in U.S. Pat. No. 2,889,363 and U.S. Pat. No. 2,889,364 (Baxter). This process starts from the naturally occurring amino acid l-tyrosine, which is iodinated in a first step to form 3,5-diiodo-l-tyrosine. The amino group is protected by acetylation in a second step and then the acid group is converted into the ethyl ester in a third step. The fourth step in this synthesis is the oxidative coupling (using oxygen and a manganese salt catalyst) of the protected iodinated tyrosine product to form a biphenyl ether moiety. Acid hydrolysis of this biphenyl ether moiety in a fifth step yields l-thyroxine, as a free base, which is converted into its sodium salt in a sixth step. The present invention relates to improvements in the preceding process.

Modern standards of pollution control, safety and environmental protection have changed over the years and it has been found that this six step synthesis, in particular the step four coupling, does not always meet modern standards. For example, pure oxygen used in an open, unpressurised system in the presence of flammable solvents is a fire or explosion hazard. Use of a pressurised closed system would be preferred to obtain greater effluent control to reduce or eliminate environmental pollution. A closed system would more readily meet modern safety standards, and reduce risk of fire. However, if the fourth step oxidative coupling reaction is performed in a closed system at increased pressure using only pure oxygen and a manganese salt, the reaction does not proceed well on a large scale even when the pressure is increased, for example to 20 atmospheres. Instead, side reactions predominate and little of the desired product is produced. An aspect of the present invention relates to a means for performing the above desired coupling reaction in reasonable yield in a closed system with all the advantages mentioned above.

At atmospheric pressure it is known the oxidative coupling step (step four) is more efficient with oxygen used as the oxidising agent than air. For example, see U.S. Pat. No. 2,589,364 (Baxter), column 4, lines 1–13, table IV—in which oxygen produces a yield of 20.8% compared to the yield with air of 4.8%. Surprisingly, it has been found that comparable or better yields are obtained in the desired coupling and the reaction time is reduced if an organic amine additive is present in the reaction mixture, the coupling is performed at a pressure of about 20 atmospheres and optionally an inert diluent is added to the oxygen. Under these conditions some or all of the disadvantages (described herein) present in the prior art process are avoided.

Broadly the invention comprises the oxidative coupling of a diiodo-l-tyrosine to form a biphenyl ether derivative, catalysed by a manganese salt in which the amine and acid functionality of the diiodo-l-tyrosine have been protected by suitable protecting groups, characterised in that the reaction is performed at a pressure of about 20 atmospheres in presence of an organic amine additive using a gaseous oxidant comprising oxygen and optionally an inert diluent.

Preferably, the inert diluent is nitrogen, and the oxidising gas mixture comprises from about 10% to 40% by volume of oxygen, more preferably from about 21% to about 38% by volume of oxygen, most preferably the gas mixture is air.

Suitably the organic amine additive may be a primary amine of formula $R_1NH_2$ in which $R_1$ comprises an optionally substituted $C_{1-10}$ alkyl chain which may be straight or branched, a secondary amine of formula $R_2R_3NH$ in which $R_2$ and $R_3$ independently represent an optionally substituted $C_{1-6}$ alkyl chain which may be straight or branched or $R_2$ and $R_3$ together with the nitrogen to which they are attached form a cyclic amine, or a tertiary amine of formula $R_4R_5R_6N$ in which $R_4$, $R_5$ and $R_6$ independently represent an optionally substituted $C_{1-6}$ alkyl chain which may be straight or branched. Preferably the organic amine additive is selected from 2-aminoethylbenzene, benzylamine, n-butylamine, cyclohexylamine, diisopropylamine, n-hexylamine, n-dodecaneamine, piperidine, morpholine, triethylamine, tributylamine and ethyl 3,5-diiodo-l-tyrosinate. More preferably the amine is selected from piperidine, morpholine, triethylamine and tributylamine. Urea or ammonia do not affect the desired coupling reaction.

Suitably the organic amine additive is present in an amount ranging from 1.2 to 5 molar equivalents with respect to the amount of manganese salt used. Preferably the organic amine additive is present in an amount ranging from 1.5 to 4 molar equivalents and more preferably in an amount ranging from 1.8 to 3.8 molar equivalents with respect to the amount of manganese salt used.

Suitably the manganese salt is present in an amount ranging from 0.25–5% by weight of the protected diiodo-l-tyrosine used, preferably 0.5–3% and more preferably 0.75–1.5% by weight of the protected diiodo-l-tyrosine used.

Surprisingly, it has been found that if air or oxygen is used in the desired coupling step at a pressure of 20 atmospheres in the presence of an organic amine additive, the yield of the coupling reaction is comparable at 35 to 45% to that obtained when oxygen is used at atmospheric pressure. A further unexpected effect is that the reaction time for the pressurised coupling in air or oxygen in the presence of an organic amine additive, is significantly reduced to 20 hours compared to 96 hours required with oxygen at atmospheric pressure. This effect is of commercial importance as it allows more efficient use of capital intensive plant equipment which results in significant cost savings compared to the current process. Air is preferred to oxygen because it is readily available, cheap and safer to use.

The amino group of the diiodo-l-tyrosine may be protected by acylation, the acid group of the diiodo-l-tyrosine may be protected by esterification.

A further aspect of the invention is the isolation of sodium 1-thyroxine from step 6 using as a starting material a thyroxine hydrochloride salt crystallised from the fifth step rather than a thyroxine free base produced from step 5. 3,5-Diiodothyronine ($T_2$), liothyronine ($T_3$) and the d-enantiomer of thyroxine (d-$T_4$) are all undesirable by products which may be formed during the synthesis of 1-thyroxine. $T_2$, $T_3$ and d-$T_4$ are biologically active and therefore it is desirable to produce an 1-thyroxine product which is substantially free of these compounds. Surprisingly, it has been discovered that if hydrochloric acid is used in the hydrolysis step five of the synthesis of thyroxine, described above, the hydrochloride salt formed contains fewer impurities of $T_2$, $T_3$ and d-$T_4$ than the free thyroxine base produced from that step. If the hydrochloride salt is the starting material for conversion into sodium 1-thyroxine (step 6), sodium 1-thyroxine is generated in greater yield and/or with fewer impurities than if the free thyroxine base is used as the starting material in step 6.

The hydrochloride salt of 1-thyroxine is a very useful intermediate in the process of the present invention and is believed to be novel. Another aspect of the present invention comprises the hydrochloride salt of 1-thyroxine in solid form. The present invention also includes the use of the hydrochloride salt of 1-thyroxine in solid form in a process for producing sodium 1-thyroxine.

Broadly, a still further aspect of the invention is a process for the synthesis of 1-thyroxine comprising the following steps:

1: Iodination of 1-tyrosine to 3,5-diiodo-1-tyrosine.
2: Protection of the amino group of the 3,5-diiodo-1-tyrosine product from step 1 with a suitable protecting group.
3: Protection of the carboxy group of the product of step 2 with a suitable protecting group.
4: Oxidative coupling of the protected 3,5-diiodo tyrosine produced from step 3 using oxygen as an oxidising agent in the presence of a manganese salt catalyst and an organic amine additive, the oxygen being diluted in a gas mixture with an inert gas diluent, the oxygen being present in an amount from 10% to 40%, by volume of the gas mixture.
5: Hydrolysis of the reaction product of step 4 with a mixture including hydrochloric acid to form the hydrochloride salt of 1-thyroxine, which is separated.
6: Formation of the sodium salt from the hydrochloride salt of 1-thyroxine produced from step 5.

A preferred process of the invention comprises the following steps:

1: Iodination of the amino acid 1-tyrosine of formula I

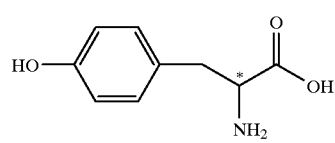

for example by treatment with NaI/NaIO$_3$ in acetic acid followed by NaHSO$_3$ to remove any excess I$_2$ to give a compound of formula II

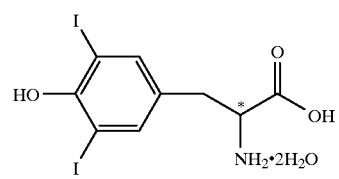

2: Acetylation of a compound of formula II with acetic anhydride and a base (eg NaOH) followed by a solution of NaOH/EtOH and finally HCl and to give a compound of formula III

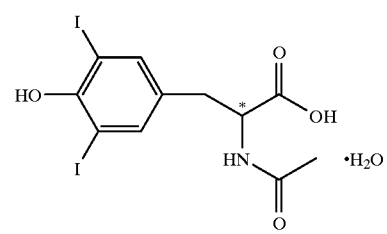

3: Esterification of compound of formula III with ethanol in sulphuric acid to give a compound of formula IV

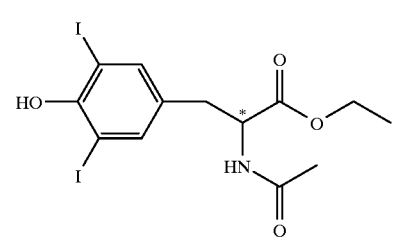

4: Oxidative coupling of a compound of formula IV using air under pressure of 20 atmospheres with MnSO$_4$ and H$_3$BO$_4$, in ethanol with a piperidine additive to form a compound of formula V

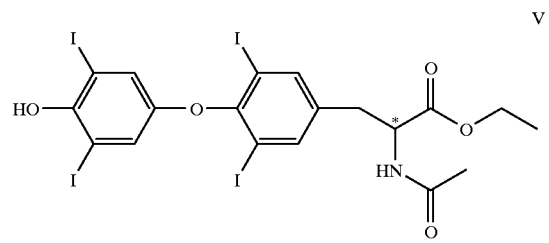

5: Hydrolysis of a compound of formula V with HCl acid and acetic acid followed by NaHSO$_3$ to produce the hydrochloride salt of formula VI

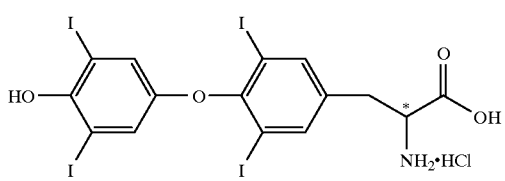

6: Reaction of the HCl salt of formula VI with $Na_2CO_3$ in a n-propanol solvent to form sodium 1-thyroxine of formula VII

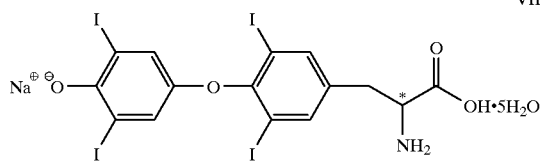

EXAMPLES 1–6 AND COMPARATIVE EXAMPLES A, B, C AND D (STEP 4)

Improvements to the fourth oxidation step are described below in more detail with reference to the following non-limiting examples 1 to 6 which are compared with control Examples A, B, C and D performed at lower pressures. The description of the process below should be read in conjunction with Tables Ia and Ib.

Ethyl N-acetyl-3,5-diiodo-1-tyrosine (i), boric acid (ii), piperidine (iii), water (iv) and ethanol (v) were charged to a preparation vessel. Caustic soda liquor (vi) of specific gravity 1.5 was added to the vessel until the initial pH of the reaction mixture was (vii). The mixture was then transferred to a pressure vessel and heated to a temperature of (viii). Water, ethanol and an aqueous solution of $MnSO_4.H_2O$ (ix) were charged to the pressure vessel. The vessel was pressurised within a range of (x) atmospheres with a gas (xi), and the reaction mixture was stirred at a temperature of (xii) for a period of (xiii) with the pressure maintained. The pH of the mixture was monitored periodically falling to a final pH of (xiv). The mixture was cooled to below 30° C. and the pressure was released. The product was collected by filtration and washed with 50% aqueous ethanol, dilute hydrochloric acid and water before being used in the fifth stage of the process. Yield (xv).

TABLE 1(A)

| Ex | Stage III Product (i) | | Boric Acid (ii) | | Piperidine (iii) | | Water (iv) | | Ethanol (v) | | NaOH (vi) | | Initial pH (vii) | Initial Temp. (viii) |
|---|---|---|---|---|---|---|---|---|---|---|---|---|---|---|
| 1 | 30.0 | kg | 0.93 | kg | 0.375 | l | 37 | l | 37 | l | 3.0 | l | 9.7 | 58° C.–62° C. |
| 2 | 29.7 | kg | 0.93 | kg | 0.375 | l | 37 | l | 37 | l | 3.1 | l | 9.5 | 57° C.–60° C. |
| 3 | 30.0 | kg | 0.93 | kg | 0.375 | l | 37 | l | 37 | l | 3.05 | l | 9.5 | 58° C.–61° C. |
| 4 | 30.0 | kg | 0.93 | kg | 0.375 | l | 37 | l | 37 | l | 3.05 | l | 9.47 | 58° C.–59° C. |
| 5 | 30.0 | kg | 0.93 | kg | 0.375 | l | 37 | l | 37 | l | 3.1 | l | 9.5 | 58° C.–60° C. |
| 6 | 200 | g | 6.2 | g | 2.5 | ml | 2 | l | 2 | l | 22 | ml | 9.5 | 58° C.–62° C. |
| A | 25 | g | 0.78 | g | 0.31 | ml | 315 | ml | 296 | ml | 2.5 | ml | 9.5 | 60° C. |
| B | 200 | g | 6.2 | g | 2.5 | l | 2 | ml | 2 | l | 23 | ml | 9.5 | 58° C.–62° C. |
| C | 265 | kg | 8.2 | kg | None | | 2681 | l | 2681 | l | 318 | l | 10.5 | 44° C. |
| D | 141 | kg | 4.4 | kg | None | | 1429 | l | 1429 | l | 170 | l | 10.5 | 44° C. |

CONTINUED as Table 1(B)

TABLE 1(B)

| Ex | $MnSO_4$ (aq) (ix) | | Pressure (atm) (min-max) (x) | Gas (xi) | Temp. of Reaction (xii) | Reaction Time (xiii) | Final pH (xix) | Yield Yield (xv) | | % Yield |
|---|---|---|---|---|---|---|---|---|---|---|
| 1 | 300 | g in 500 ml $H_2O$ | 19.6–20.1 | $O_2$ (a) | 58° C.–62° C. | 20 hrs | 7.13 | 10.6 | kg | 39.3 |
| 2 | 300 | g in 500 ml $H_2O$ | 19.7–20.1 | $O_2$ (a) | 58° C.–62° C. | 20 hrs | 6.8 | 11.3 | kg | 41.7 |
| 3 | 300 | g in 500 ml $H_2O$ | 19.8–20.3 | Air (a) | 58° C.–62° C. | 20 hrs | 7.18 | 11.2 | kg | 41.5 |
| 4 | 300 | g in 500 ml $H_2O$ | 19.6–20.1 | Air (a) | 58° C.–62° C. | 20 hrs | 7.25 | 9.7 | kg | 35.8 |
| 5 | 300 | g in 500 ml $H_2O$ | 19.7–20.2 | 15.7 atm $N_2$ 5.3 atm $O_2$ (b) | 58° C.–62° C. | 20 hrs | 7.15 | 12.2 | kg | 43.1 |
| 6 | 2 | g in 10 ml $H_2O$ | 19–20 | Air | 58° C.–62° C. | 21 hrs | 7.5.5 | 64.2 | g | 33.2 |
| A | 0.25 | g in 1 ml $H_2O$ | 5 | Air | 60° C. | 20 hrs | 7.64 | 7.3 | g | 33.2 |
| B | 2 | g in 10 ml $H_2O$ | 5 | Air | 60° C. | 20 hrs | 8.6 | 10.9 | g | 5.6 |

TABLE 1(B)-continued

| Ex | MnSO$_4$ (aq) (ix) | Pressure (atm) (min-max) (x) | Gas (xi) | Temp. of Reaction (xii) | Reaction Time (xiii) | Final pH (xix) | Yield Yield (xv) | % Yield |
|---|---|---|---|---|---|---|---|---|
| C | 5.3 kg in 7.6 l H$_2$O | Atmospheric | O$_2$ | 44° C. | 96 hrs | 7.75 | 100.8 kg | 44.7 |
| D | 2.8 kg in 3.8 l H$_2$O | Atmospheric | O$_2$ | 44° C. | 96 hrs | 7.72 | 38.7 kg | 50.7 |

Footnotes to Table 1B
(a) On average the reaction pressure was maintained at 20 bar by this gas.
(b) On average the reaction pressure was maintained at 20 bar by this gas mixture then released after 8 hours and repressurised on average to 20 bar with air for a further 12 hours.

EXAMPLES 7 TO 15 AND COMPARATIVE EXAMPLE E (STEP 5)

Improvements to step 5 (hydrolysis of the product of step 4) will now be illustrated with reference to the following non-limiting Examples 7 to 15 and Table 2:

The product that was obtained from step 4 (in a method similar to that described above) in an amount of (a), was heated under reflux with acetic acid (b), hydrochloric acid (c) and water (d) at a temperature of (e) for a period of (f). The reaction mixture was cooled to (g) and sodium bisulphite solution was added to remove free I$_2$. The solid product was isolated by filtration, washed with water and dried. Yield (h) of the thyroxine hydrochloride salt. The impurities T$_2$ (j), T$_3$ (k) and d-T$_4$ (l) were characterised by high performance liquid chromatography (hplc).

A comparative example E was prepared as above except that NaOH was added after washing the solid to generate 1-thyroxine (as a free base) which was isolated. Impurities were also characterised by hplc.

EXAMPLES 16 TO 19 AND COMPARATIVE EXAMPLES F AND G (STEP 6)

Improvements in the yield and purity of the sodium salt of 1-thyroxine generated in step 6 are illustrated in Table 3. The product of step 5 (free base or HCl salt) was treated with sodium carbonate in a n-propanol solvent to generate sodium 1-thyroxine which was isolated by filtration. Table 3 shows that if the starting material of step 6 is a hydrochloride salt of 1-thyroxine, (Examples 16 to 19), then sodium 1-thyroxine is generated in higher yield and/or with less impurities than if the free thyroxine base is used as the starting material as in the prior art process (as in comparative examples F and G). The impurities were characterised by hplc.

TABLE 3

| Example | Starting material (from step 5) | Amount of starting material | % Yield of Na 1-thyroxine | % Impurities (characterised by hplc) | | |
|---|---|---|---|---|---|---|
| | | | | T$_2$ | T$_3$ | d-T$_4$ |
| 16 | HCl salt of T$_4$ | 3.5 g | 84.0 | 0 | 0.4 | 0.5 |
| 17 | HCl salt of T$_4$ | 7.0 g | 87.6 | 0 | 0.2 | 0.3 |
| 18 | HCl salt of T$_4$ | 5.0 kg | 73.8 | 0 | 0.6 | 0.7 |
| 19 | HCl salt of T$_4$ | 5.0 kg | 73.1 | 0 | 0.5 | 0.3 |

TABLE 2

| Ex | Prod. IV (a) | Acetic Acid (b) | HCl Acid (c) | Water (d) | Reflux Temp (d) | Reflux Time (f) | Cooled Temp (g) | Yield (h) | Impurities (%) T$_2$ (j) | T$_3$ (k) | d-T$_4$ (l) |
|---|---|---|---|---|---|---|---|---|---|---|---|
| 7 | 10 kg | 50 l | 8 l | 20 l | 103° C.–104° C. | 5 hrs | 20–25° C. | 8.7 kg 91.8% | 0% | 0.4% | 0.3% |
| 8 | 10 kg | 50 l | 8 l | 20 l | 106° C.–107° C. | 5 hrs | 20–25° C. | 8.5 kg 93.6% | 0% | 0.5% | 0.4% |
| 9 | 10 kg | 50 l | 8 l | 20 l | 107° C.–109° C. | 5 hrs | 20–25° C. | 9.0 kg 94.7% | 0% | 0.5% | 0.3% |
| 10 | 9.5 g | 77 ml | 31 ml | 10 ml | 105° C.–110° C. | 3 hrs | 25° C. | 7.92 g | <0.1% | 0.4% | 0.3% |
| 11 | 10 g | 81 ml | 33 ml | 11 ml | 105° C.–110° C. | 3 hrs | 25° C. | 8.38 g | <0.1% | 0.4% | 0.3% |
| 12 | 10 g | 81 ml | 33 ml | 11 ml | 105° C.–110° C. | 5 hrs | ambient | 8.53 g | 0% | 0.6% | 0.6% |
| 13 | 10 g | 81 ml | 33 ml | 11 ml | 105° C.–110° C. | 5 hrs | ambient | 8.78 g | 0% | 0.4% | 0.4% |
| 14 | 10 g | 81 ml | 33 ml | 11 ml | 105° C.–110° C. | 5 hrs | ambient | 8.70 g | 0% | 0.5% | 0.5% |
| 15 | 10 g | 81 ml | 33 ml | 11 ml | 105° C.–110° C. | 5 hrs | ambient | 8.43 g | 0% | 0.6% | 0.6% |
| E | 60.3 kg | 486 l | 199 l | 66 l | 105° C.–110° C. | 5 hrs | 20–25° C. | 53.6 kg | 1.1% | 2.7% | 1.1% |

TABLE 3-continued

| Example | Starting material (from step 5) | Amount of starting material | % Yield of Na 1-thyroxine | % Impurities (characterised by hplc) | | |
|---|---|---|---|---|---|---|
| | | | | $T_2$ | $T_3$ | $d-T_4$ |
| F | Free $T_4$ base | 92 kg | 74.9 | 0 | 1.3 | 1.5 |
| G | Free $T_4$ base | 122 kg | 73.9 | 0 | 0.7 | 1.2 |

I claim:

1. A process comprising the oxidative coupling of a diiodo-l-tyrosine catalyzed by a manganese salt in which the amine and acid functionality of the diiodo-l-tyrosine have been protected by suitable protecting groups to form a biphenyl ether derivative of formula VI

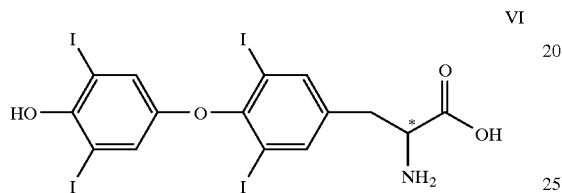

in which the amine and the acid functionality are protected by suitable protecting groups, wherein the reaction is carried out at a pressure of about 20 atmospheres in the presence of an organic amine additive selected from the group consisting of 2-aminoethylbenzene, benzylamine, n-butylamine, cyclohexylamine, diisopropylamine, n-hexylamine, n-dodecaneamine, piperidine, morpholine, triethylamine, tributylamine and ethyl 3,5-diiodo-l-tyrosinate using a gaseous oxidant comprising oxygen and optionally an inert diluent.

2. A process as claimed in claim 1 further comprising acid hydrolysis of the biphenyl ether derivative with hydrochloric acid to form a l-thyroxine hydrochloride salt and generation of sodium-l-thyroxine from the l-thyroxine hydrochloride salt.

3. A process for preparing sodium l-thyroxine comprising the following steps:
   (a) iodination of l-tyrosine to 3,5-diiodo-l-tyrosine;
   (b) protection of the amino group of the 3,5-diiodo-l-tyrosine product from step (a) with a suitable protecting group;
   (c) protection of the carboxy group of the product of step (b) with a suitable protecting group;
   (d) oxidative coupling of the protected 3,5-diiodo tyrosine produced from step (c) using oxygen as an oxidizing agent in the presence of a manganese salt catalyst and an organic amine additive selected from the group consisting of 2-aminoethylbenzene, benzylamine, n-butylamine, cyclohexylamine, diisopropylamine, n-butylamine, cyclohexylamine, diisopropylamine, n-hexylamine, n-dodecaneamine, piperidine, morpholine, triethylamine, tributylamine and ethyl 3,5-diiodo-l-tyrosinate, the oxygen being diluted in a gas mixture with an inert gas diluent, the oxygen being present in an amount from 10% to 40%, by volume of the gas mixture;
   (e) hydrolysis of the reaction product of step (d) with a mixture including hydrochloric acid to form the hydrochloride salt of l-thyroxine, which is separated;
   (f) formation of the sodium salt from the hydrochloride salt of l-thyroxine produced from step (e).

4. A process as claimed in claim 1 comprising the following steps:
   (a) iodination of the amino acid l-tyrosine of formula I

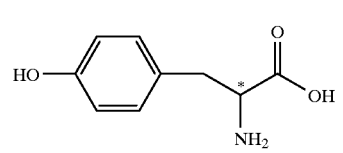

followed by removal of any excess $I_2$, to give a compound of formula II

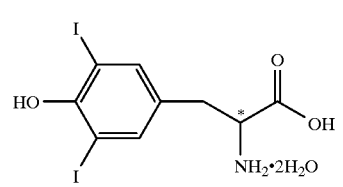

(b) acetylation of a compound of formula II with acetic anhydride and a base to give a compound of formula III

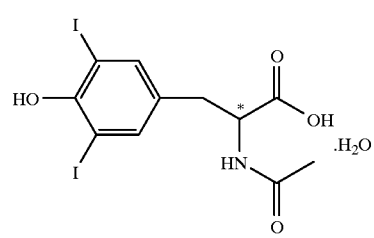

(c) esterification of compound of formula III with ethanol in sulphuric acid to give a compound of formula IV

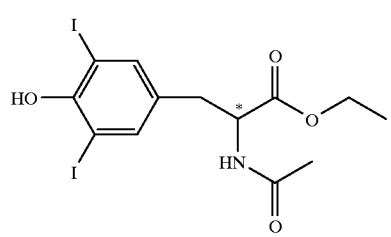

(d) oxidative coupling of a compound of formula IV using air under pressure of 20 atmospheres with $MnSO_4$ and $H_3BO_4$ in ethanol with a piperidine additive to form a compound of formula V

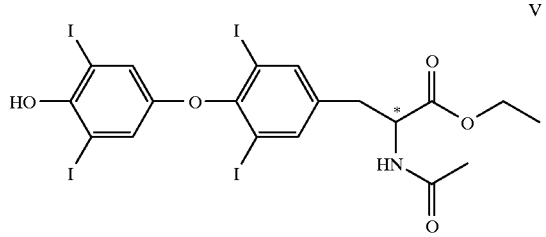

(e) hydrolysis of a compound of formula V with hydrochloric acid to produce the hydrochloride salt of formula VI

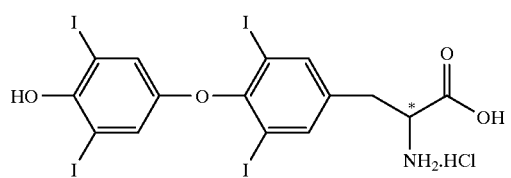

(f) reaction of the hydrochloric salt of formula VI with a sodium base to form sodium l-thyroxine of formula VII

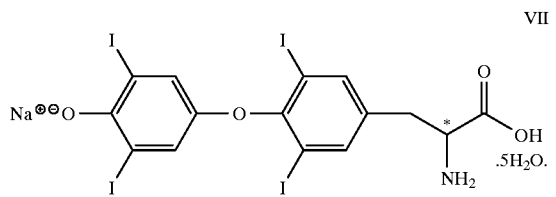

5. A process according to claim 1 in which the organic amine is a member selected from the group consisting of piperidine, morpholine, triethylamine and tributylamine.

6. A process according to claim 3 in which the organic amine is a member selected from the group consisting of piperidine, morpholine, triethylamine and tributylamine.

7. A process according to claim 1 in which the gaseous oxidant is air.

8. A process according to claim 1 in which the manganese salt is present in an amount ranging from 0.25–5% by weight of the protected diiodo-l-tyrosine used.

9. A process according to claim 1 in which the organic amine additive is present in an amount ranging from 1.2 to 5 molar equivalents with respect to the amount of manganese salt used.

10. A process according to claim 1 wherein the amino group of the diiodo-l-tyrosine is protected by acylation.

11. A process according to claim 1 in which the acid group of the diiodo-l-tyrosine is protected by esterification.

12. A process according to claim 1, wherein the reaction is carried out at a pressure in the range of from 19.6 to 20.3 atmospheres.

13. A process for producing sodium l-thyroxine comprising reacting the hydrochloride salt of l-thyroxine in solid form with $Na_2CO_3$ in n-propanol solvent until sodium l-thyroxine is formed, and then recovering the sodium l-thyroxine.

* * * * *

UNITED STATES PATENT AND TRADEMARK OFFICE
CERTIFICATE OF CORRECTION

PATENT NO. : 5,917,087
DATED : June 29, 1999
INVENTOR(S) : COE et al.

It is certified that error appears in the above-identified patent and that said Letters Patent is hereby corrected as shown below:

```
On the title page, item [75] Inventor, should read
-- Paul Frederick Coe; Andrew Timothy Turner, both of Nottingham, United
   Kingdom --
```

Signed and Sealed this

Twenty-eighth Day of March, 2000

*Attest:*

*Attesting Officer*

Q. TODD DICKINSON

*Commissioner of Patents and Trademarks*